(12) United States Patent  (10) Patent No.: US 9,220,627 B2
Fisher  (45) Date of Patent: Dec. 29, 2015

(54) ABDOMINAL ELEVATOR

(76) Inventor: Mark Allen Fisher, Farmington, NM (US)

( * ) Notice: Subject to any disclaimer, the term of this patent is extended or adjusted under 35 U.S.C. 154(b) by 66 days.

(21) Appl. No.: 13/308,149

(22) Filed: Nov. 30, 2011

(65) Prior Publication Data

US 2013/0133668 A1    May 30, 2013

(51) Int. Cl.
*A61F 5/03*    (2006.01)
*A61F 5/37*    (2006.01)
*A61B 17/02*   (2006.01)

(52) U.S. Cl.
CPC ............... *A61F 5/03* (2013.01); *A61F 5/3776* (2013.01); *A61B 17/02* (2013.01); *Y10T 156/1093* (2015.01)

(58) Field of Classification Search
CPC ........... A61F 5/03; A61F 5/37; A61F 5/3776; A61F 5/3784; A61B 17/02; A61B 17/0281; A61B 2017/0212; A61B 2017/0287
USPC ................... 128/845, 849, 851; 600/201, 206
See application file for complete search history.

(56) References Cited

U.S. PATENT DOCUMENTS

| | | | |
|---|---|---|---|
| 4,310,509 A | 1/1982 | Berglund et al. | |
| 4,323,557 A | 4/1982 | Rosso et al. | |
| 4,452,845 A | 6/1984 | Lloyd et al. | |
| 4,489,720 A | 12/1984 | Morris et al. | |
| RE31,886 E | 5/1985 | Hodgson | |
| RE31,887 E | 5/1985 | Hodgson | |
| 4,619,253 A | 10/1986 | Anhauser et al. | |
| 5,599,289 A | 2/1997 | Castellana | |
| 5,979,450 A | 11/1999 | Baker et al. | |
| 5,985,395 A | 11/1999 | Comstock et al. | |
| 6,187,126 B1 | 2/2001 | Rothrum et al. | |
| 6,742,522 B1 * | 6/2004 | Baker et al. | 128/849 |
| 7,455,649 B2 * | 11/2008 | Root et al. | 602/19 |
| 7,938,121 B2 | 5/2011 | McKnight et al. | |
| 2005/0150503 A1 | 7/2005 | Votel | |
| 2007/0232864 A1 * | 10/2007 | Sharp et al. | 600/227 |
| 2009/0264709 A1 * | 10/2009 | Blurton et al. | 600/206 |
| 2010/0145155 A1 | 6/2010 | Sorajja | |
| 2010/0318013 A1 | 12/2010 | Fabo et al. | |
| 2012/0024296 A1 * | 2/2012 | Long Sharps et al. | 128/845 |

OTHER PUBLICATIONS

Traxi Panniculus Retractor, Product and Ordering Information, Clinical Innovations, Murray, Utah 84123, published 2015.

* cited by examiner

*Primary Examiner* — Alireza Nia
*Assistant Examiner* — Keri J Nelson
(74) *Attorney, Agent, or Firm* — Wagner Law LLC

(57) ABSTRACT

The abdominal elevator comprises a body portion made from a flexible foam, a polymer, paper or fabric having at least one upper edge and, optionally, two or more side edges, with a shape ranging from triangular to rectangular to oval with one or more straps attached to one or more of the edges and also having an anterior surface and a posterior surface having a adhesive applied to the posterior surface. The straps of the abdominal elevator are attached to the bedrail using a secure method that comfortably elevates, retracts and retains the abdominal pannus during a surgical procedure that requires access to the lower abdomen and/or groin area that would otherwise be obstructed.

18 Claims, 6 Drawing Sheets

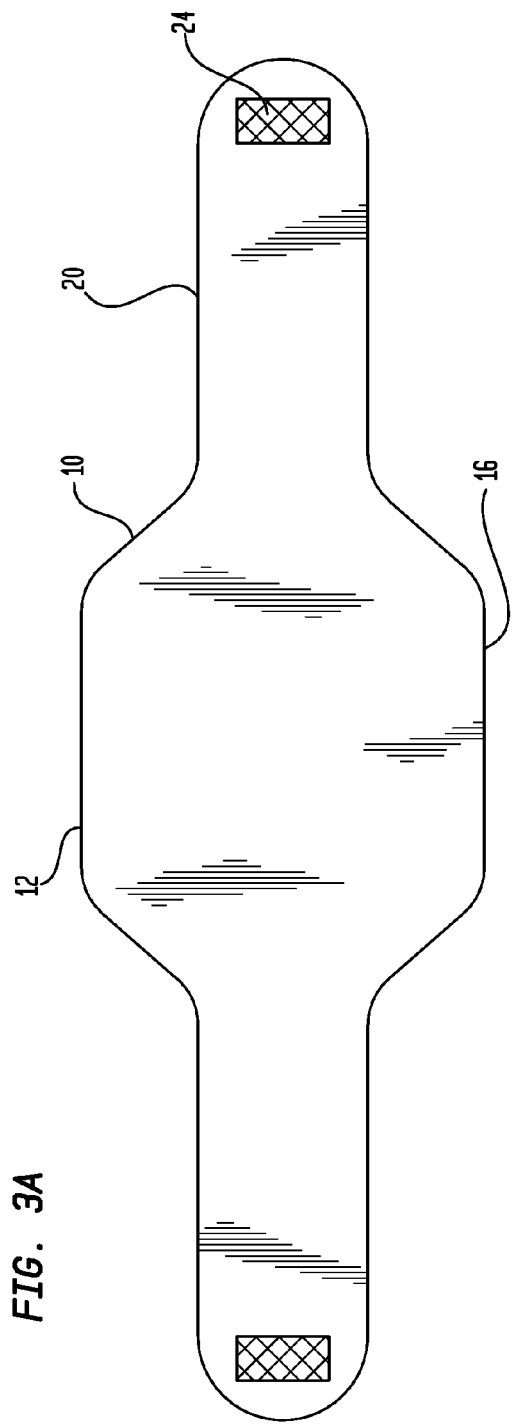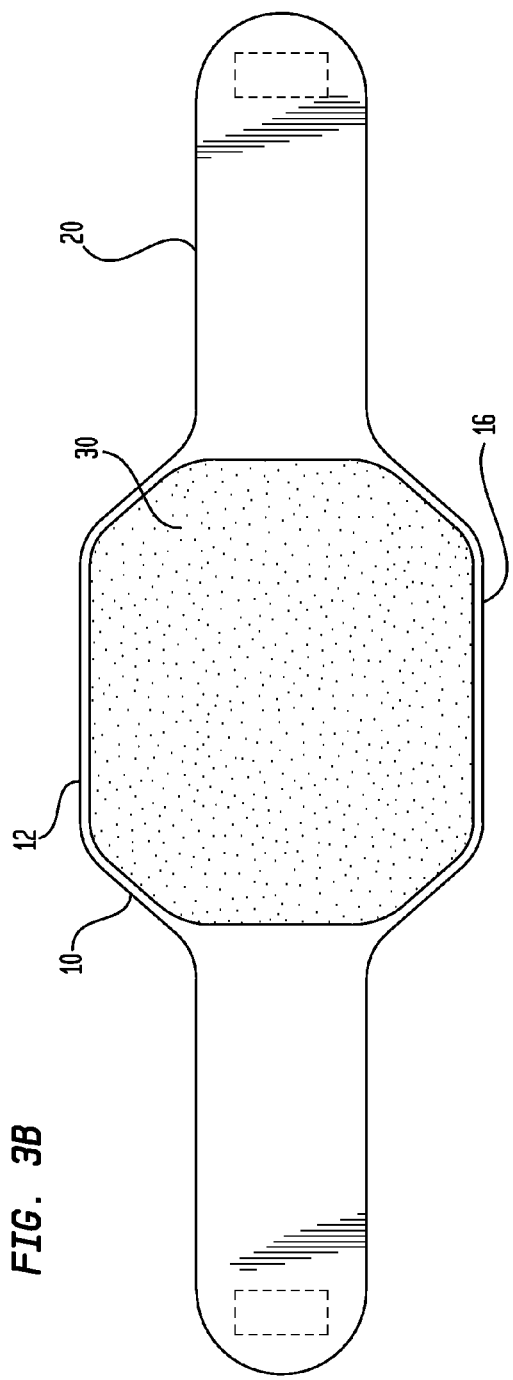
FIG. 3A
FIG. 3B

ABDOMINAL ELEVATOR

FIELD OF THE INVENTION

The present invention relates generally to the field of medical and surgical devices, and in particular to a sterile pannus retractor that is well suited for use in the performance of a surgical procedure requiring access to the abdomen or groin area in the morbidly obese.

BACKGROUND

Obesity is an epidemic in the United States. It presents health risks, which often requires more medical care. In addition to the need for increased care, the size and shape of the body impacts the quality of medical care. This is particularly true for medical procedures that require access to the abdomen or groin area when the patient has developed a pannus.

A pannus is a region of loose skin and fatty tissue in the lower abdomen. It descends below the abdomen and appears as an apron often obscuring the abdomen and groin area due to its lack of musculature and mass. It can be a serious obstacle for any doctor that is attempting to examine, treat or otherwise access that area of the patient, particularly in surgical procedures such as a cesarean section. Further, when the doctor is performing a surgical procedure, it is necessary that it be done in a sterile environment and preferably with devices that maintain and encourage a sterile environment, particularly at an incision site.

Current operating room procedures for handling a pannus are limited and ineffectual, particularly for cesarean sections. In some instances, the pannus is restrained using tape to lift it out of the groin region. The tape attaches the pannus to the body itself or attaches to the bedrail. The tape is several strips running along the body. This is not comfortable to the patient and the practice is unreliable as the tape is unable to reliably maintain the retraction under the weight of the pannus, which often releases itself during the procedure, making it difficult to maintain sterility of the surgical field. The sudden release of the pannus is also dangerous as it may obstruct the incision site as the physician is performing the procedure. Other times, medical professionals simply proceed with the medical procedure while attempting to work around, over, and through the pannus. This is also dangerous as a large pannus significantly obscures the view. And, as with the makeshift taping practice, it presents issues with maintaining sterility as the medical professional is forced to interact with parts of the body that are not necessarily a part of the surgical field.

Many surgical procedures employ a surgical incise drape to maintain sterility. Typically, the surgical area of the patient is cleaned and treated with an antimicrobial. The surgical site is then squared-off using a surgical drape that has an opening that is larger than the expected size of the incision. An incise material is then used to cover all or a portion of the patient's skin left exposed by the surgical drape. The incise material helps to reduce the migration of germs into the incision site. This is necessary because the skin's pores still contain germs and bacteria that can migrate to the surface as the skin is moved and worked during the course of a surgical procedure despite cleansing of the skin. By covering the skin with incise material, a lower incidence of surgical site contamination occurs.

Surgical incise drapes are well known in the art. In their simplest form, they are a clear polymeric body portion with an adhesive on one side that is covered by a release liner. There are two suppliers of incise drapes: Minnesota Mining and Manufacturing Company, St. Paul, Minn., and T. J. Smith and Nephew Ltd. Examples of incise material can be found in U.S. Pat. Nos. 4,310,509; 4,323,557; 4,452,845; Re. 31,886; and Re. 31,887. These incise drapes, however, function strictly to provide a sterile environment. They have no functionality for retraction of a pannus.

U.S. Pat. No. 7,938,121 provides an abdominal restraint (tension band) that includes a base and a support. The abdominal restraint may include a lateral member that is selectively attachable to a longitudinal member that may be attached to an operating or examining table. This device presents challenges. First, it does not provide protection from contamination from bacteria that can be found on other portions of the patient's body or that may be airborne or conveyed by the surgical staff. Second, given that the abdominal restraint is made of an opaque tension band, it may interfere with the incise site or obscure the doctors view. U.S. Publication 20100145155 discloses a garment in the shape of a girdle or athletic shorts with apertures on the front of the garment such that the apertures expose the inguinal regions of a patient. The garment may include an upper portion that allows for retraction of the pannus. This device is also problematic as it works as a garment, inhibiting access to certain incision sites. It is also problematic as it is difficult to dress and undress the patient, particularly after a surgical procedure.

As such, there is a need for a pannus retraction device that can retract and retain the pannus from the lower abdominal/groin area and maintain sterility while the medical professional exams or treats the patient. The retractor should be flexible and elastomeric to provide comfort to the patient. The retractor should also allow the physician to cut though it if necessary. The present invention serves these purposes.

The abdominal elevator of the present invention retracts and retains the pannus while providing a completely sterile field with an unobstructed view of the incision site. The abdominal elevator comprises a body portion made from a flexible foam, paper, polymer, or fabric having at least one upper edge and, optionally, two or more side edges, with a shape ranging from triangular to rectangular to oval with one or more straps attached to one or more of the edges and also having an anterior surface and a posterior surface having a adhesive applied to the posterior surface. The abdominal elevator of the present invention is flexible and comfortable for the patient.

SUMMARY OF THE INVENTION

The present invention is a surgically sterile pannus retractor. The abdominal elevator (100) comprises a body portion (10) made from a sterile flexible foam, paper, a polymer, or fabric having at least one upper edge (12) and, optionally, two or more side edges (14) and a bottom edge (16), with a shape ranging from triangular to rectangular to oval with one or more straps (20) attached to one or more of the edges (12 and/or 16) and also having an anterior surface (18*a*) and a posterior surface (18*b*) having an adhesive (30) applied to the posterior surface (18*b*). In one embodiment, sterility is enhanced by applying an adhesive having antimicrobial activity.

In one embodiment, the device has a triangular shape with a strap attached to the apex. In another embodiment, the device has two side edges with a strap attached to each of the left and right edges. In yet another embodiment, the device has a strap attached to the apex, as well as each of the left and right sides. In yet another embodiment, the strap may be continuous with the body of the device forming a narrower portion. The strap may be made from any of paper, a polymer or cloth or of the same material as the body portion when it is continuous therewith.

The body portion of the device has an anterior surface and posterior surface. An adhesive layer may be applied to the posterior surface of the body portion. The adhesive layer is any medical grade adhesive that allows for secure attachment of the body portion to the pannus. Further, the adhesive is pressure sensitive such that it attaches easily to the pannus with gentle pressure by the medical professional. The body portion of the device may also be formed entirely from a polymer membrane that is transparent and would allow for visualization of the underlying skin and may also be cut through if so desired.

The abdominal elevator is shaped such that it can be applied to the pannus via the adhesive layer. After placement of the abdominal elevator, light to moderate traction is applied to the abdominal wall via the strap(s) causing elevation of the pannus. The strap of the abdominal elevator is secured to the bedrail in a place that does not obstruct the incision site. It may be secured either at the superior end of the bed on the rail above the shoulder of the patient or at the side of the bed on the rail(s) along the sides of the patient.

The abdominal elevator is sterile as it is used in surgical procedures. In one embodiment, sterility is achieved by forming the device from sterile material such as a polymer composition having an antimicrobial component. In another embodiment, the adhesive layer contains an antimicrobial. In yet another embodiment, the abdominal elevator is sterilized through an acceptable process such as ethylene oxide, gamma irradiation, or electron beam radiation. One skilled in the art will recognize that one or all of the methods for creating a sterile device may be used. The abdominal elevator provides more adequate exposure to the operative field than other devices or procedures for retracting the pannus.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 3A is an anterior view of the abdominal elevator having a rectangular shape with continuous straps and connectors (Velcro);

FIG. 3B is posterior view of the abdominal elevator having a rectangular shape with continuous straps showing the adhesive layer on the body portion;

DETAILED DESCRIPTION

Figure 2A:
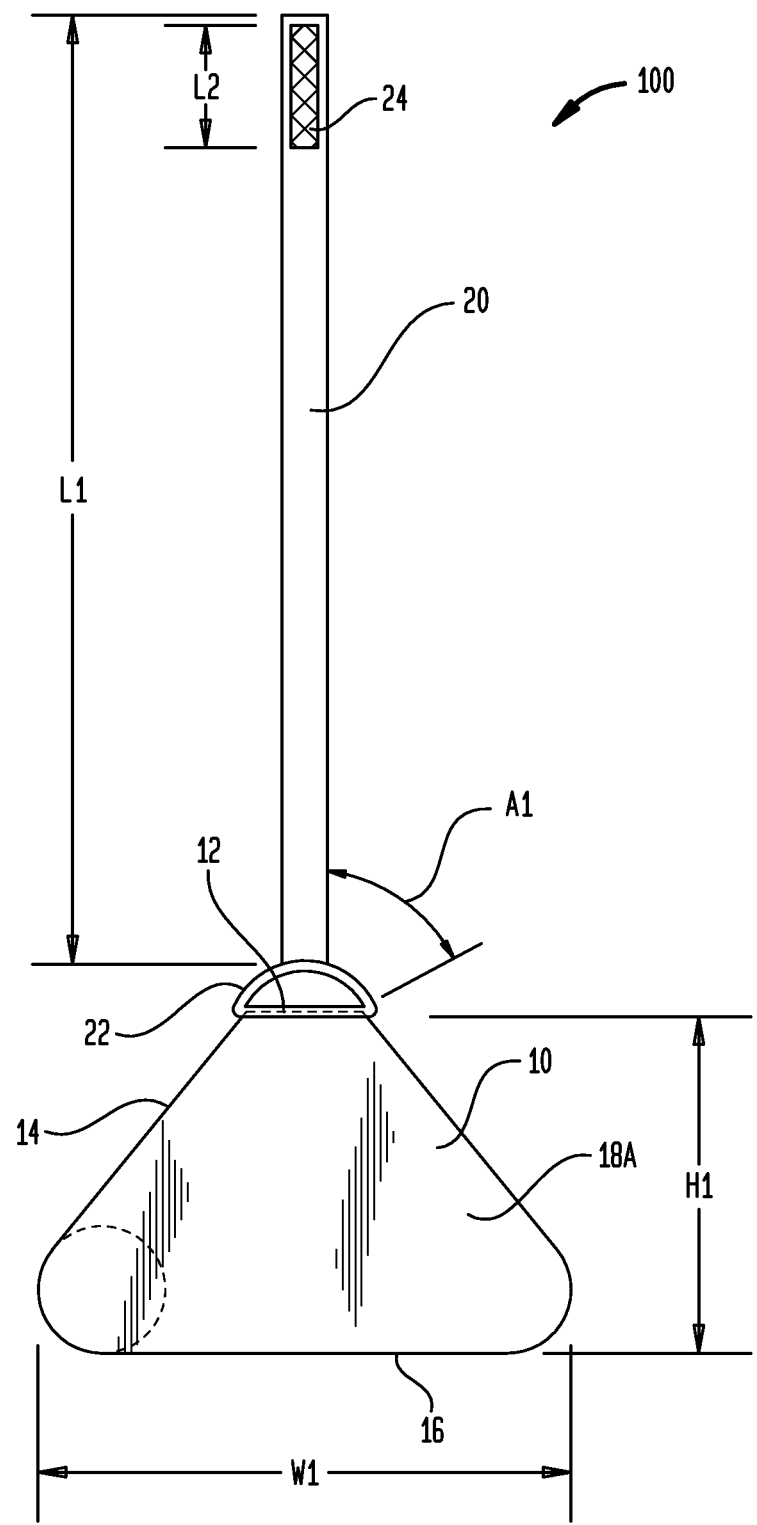
FIG. 2A is a front view of the abdominal elevator having one strap on the superior edge and showing connectors (Velcro) at distal end of strap.
Figure 2B:
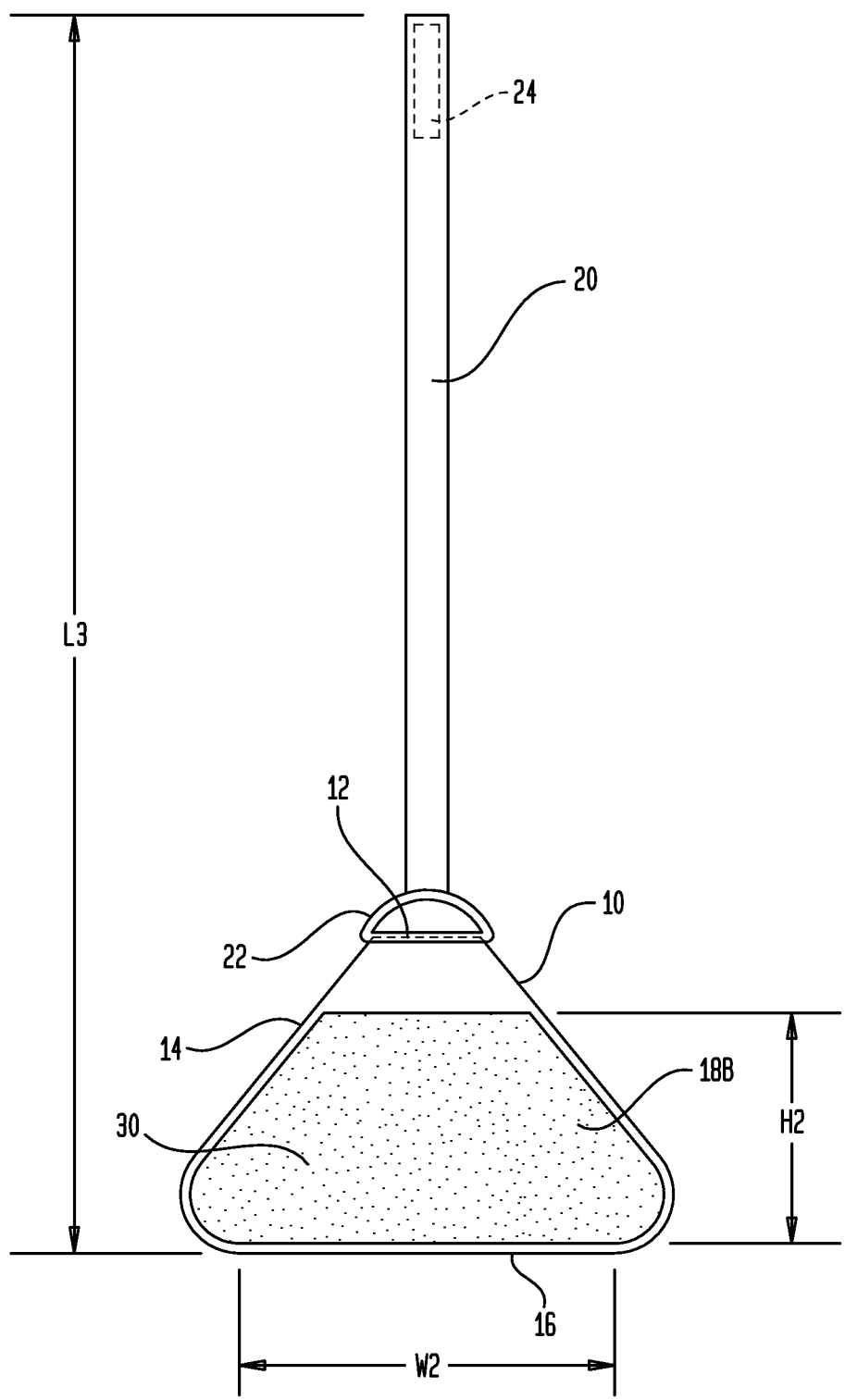
FIG. 2B is posterior view of the abdominal elevator having one strap on the upper edge showing the adhesive layer on the body portion.

As shown in FIGS. 2A and 2B, the present invention relates to a surgically sterile pannus retractor (100), which is well suited for use in the performance of a cesarean section in the morbidly obese. The abdominal elevator (100) comprises a flexible body portion (10) having at least one upper edge (12), or optionally two or more side edges (14) and a bottom edge (16), with one or more straps (20) attached to one or more of the edges (12 and/or 14), wherein the straps have one or more attachers (24) such as Velcro, adhesive, buttons or snaps, and the body portion also having an anterior surface (18a) and a posterior surface (18b) having an adhesive (30) applied to the posterior surface (18b), and optionally, a release sheet (not shown) applied thereto.

The flexible body portion (10) of the abdominal elevator (100) may be any size or shape that allows it to fit securely onto the pannus such that the pannus can be retracted and retained using the strap(s) (20) attached to the body portion (10) of the device. The body portion (10) may any geometric shape that can contain the pannus selected from the group consisting of a triangle, rectangle, hexagon, oval or some other geometric shape that securely contains the pannus. Preferably, the geometric shape has rounded edges or corners to make the abdominal elevator more comfortable to the patient such as a triangle with rounded edges or a rectangle with rounded edges as shown in FIGS. 2A, 2B, 3A, and 3B. As an example of an abdominal elevator (100) as shown in FIG. 2A, the body portion (10) of the abdominal elevator (100) has a width (W1) that is sufficient to contain the pannus. Preferably, the width (W1) is about 50 to 100 cm. Most preferably, the width (W1) is about 50 to 60 cm. The body portion (10) of the abdominal elevator (100) has a height (H1) that is sufficient to contain the pannus. Preferably, the height (H1) is about 20 to 80 cm. Most preferably, the height (H1) is about 30 cm to 40 cm.

The body portion (10) may be made from any material that is strong and durable enough to contain and restrain the weight of the pannus. It may be selected from the group consisting of foam, paper, a polymer or cloth. When the body portion (10) is a polymer, the polymer may be selected from the group consisting of polyethylenes, polyurethanes, polyesters and polyamides. Preferably, the body portion (10) is elastomeric such that it more easily conforms to the pannus. The body portion (10) may also be formed from a transparent material that allows for visualization of the underlying skin and may also be cut through if so desired. The body portion (10) is thick enough to maintain its form when applied to the pannus and resists tearing, yet it is thin enough to be comfortable to the patient and cut through if necessary. The body portion (10) may also have antimicrobial properties. The antimicrobial properties may be achieved by forming the body portion from foam, paper, a polymer or cloth having an antimicrobial component or sterilization of the body portion (10).

Figure 4A:
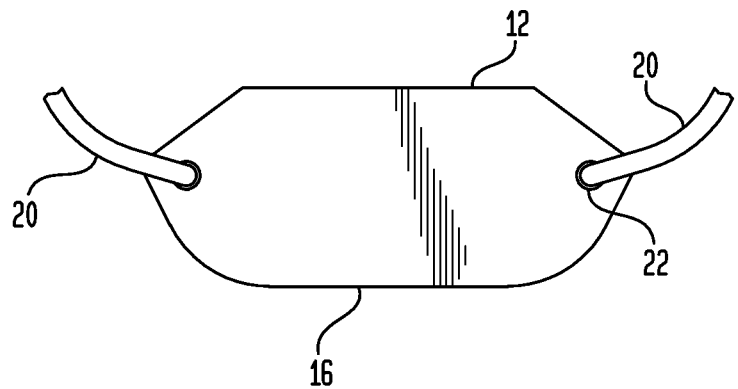
FIGS. 4A, 4B and 4C is an anterior view of the abdominal elevator in various geometric shapes with various numbers of straps and connectors (snaps).
Figure 4B:
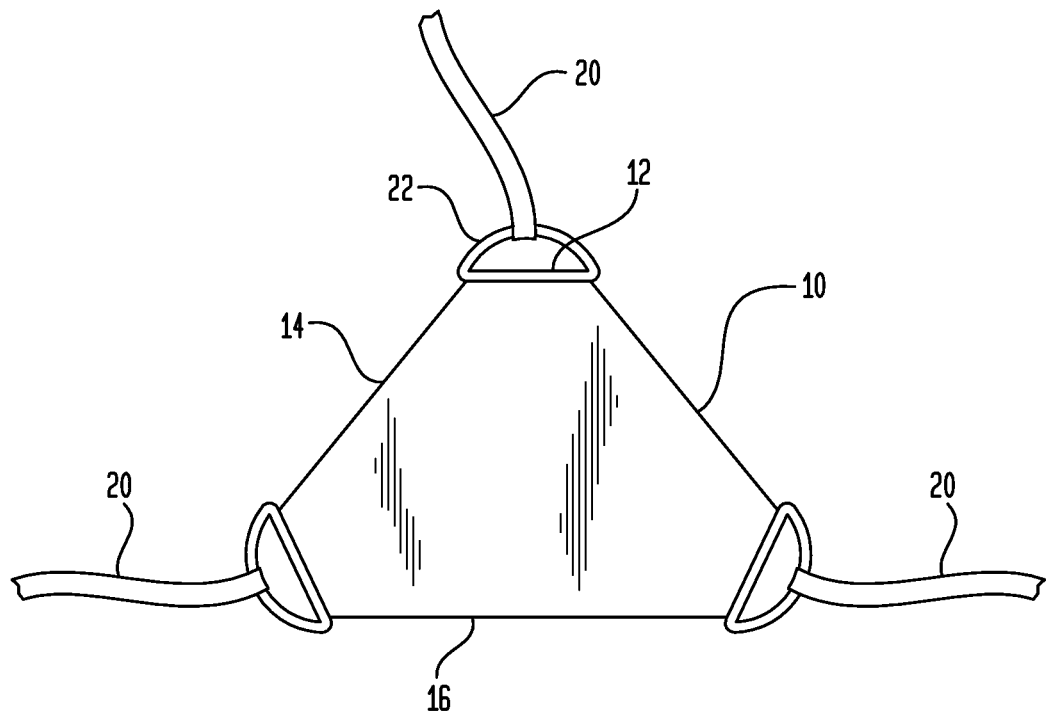
Figure 4C:
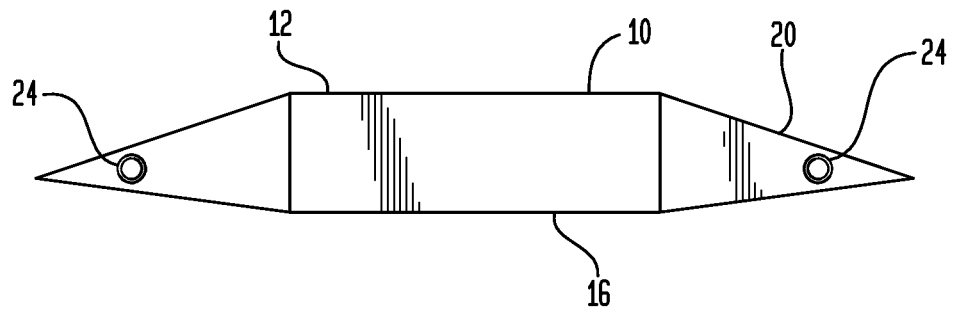

One or more straps (20) may attached to the body portion (10) at either the upper edge (12) of the body portion (10) as shown in FIGS. 2A and 2B or on each side (14) as shown in FIGS. 4A, 4B and 4C. The straps (20) are made of any sturdy material that maintains sterility and comfort for the patient. The straps (20) may be made of foam, paper, a polymer or cloth. The strap has a length (L1) that is long enough to connect the abdominal elevator (100) to the bedrail while retaining the pannus. The strap (20) may be 140 to 170 cm in length (L1). One skilled in the art will recognize that the length (L1) of the strap (20) is adjustable based upon the attachment method to the body portion (10) and the bedrail.

The straps (20) may be attached to the body portion (10) by any method that reliably secures it including welding, gluing, tying, sewing or with a connector (22). The connector (22) may be selected from the group consisting of D rings, O rings and square rings. Alternatively, the device (100) may be formed such that the strap (20) is continuous with the body portion (10) as shown in FIGS. 3A and 3B. The strap (20) may also contain an attacher (24) such as snaps, buttons, Velcro or an adhesive for securing the strap (20) to itself at either the proximal or distal end. When the attacher (24) is Velcro or an adhesive, the length (L2) is sufficient to allow the attacher (24) to securely attach to the strap (20) or at to a compliment (not shown) along the strap (20). The length (L2) is about 4 to 10 cm. Preferably, the length is about to 8 cm. Most preferably, the length is about 6 to 7 cm.

The body portion (10) of the device has an anterior surface (18a) and posterior surface (18b). An adhesive layer (30) may be applied to the posterior surface (18b) of the body portion (10) of device. As shown in FIGS. 2B and 3B, the adhesive is applied to a major portion of the posterior surface (18b) of the body portion (10). Preferably, it is applied to a height (H2) that is 50% to 98% of the total height of the body form (10). Most preferably, the height (H2) is no more than 75% of the body form (10), such that the pannus is securely retracted yet the abdominal elevator (100) is more comfortably removed from the patient upon completion of the surgical procedure.

The adhesive (30) may be any that is suitable for medical purposes and that allows secure attachment of the abdominal elevator (100) to the pannus. Preferably, the adhesive (30) is a pressure sensitive adhesive. The adhesive (30) may also contain an antimicrobial such as iodine, phenols, fatty acid monoesters, silver, and silver salts, and hydrogen peroxide. The adhesive (30) may be applied by spraying, painting or laminating.

Figure 1B:
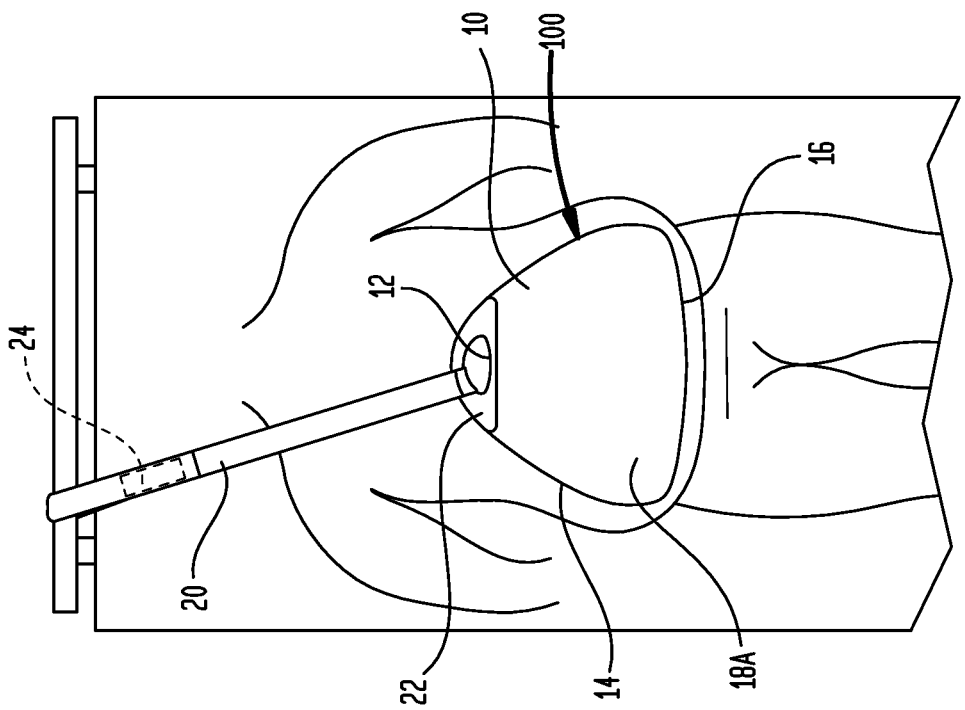
FIG. 1B is a perspective view of the abdominal elevator on a patient exposing the incision site.
Figure 1A:
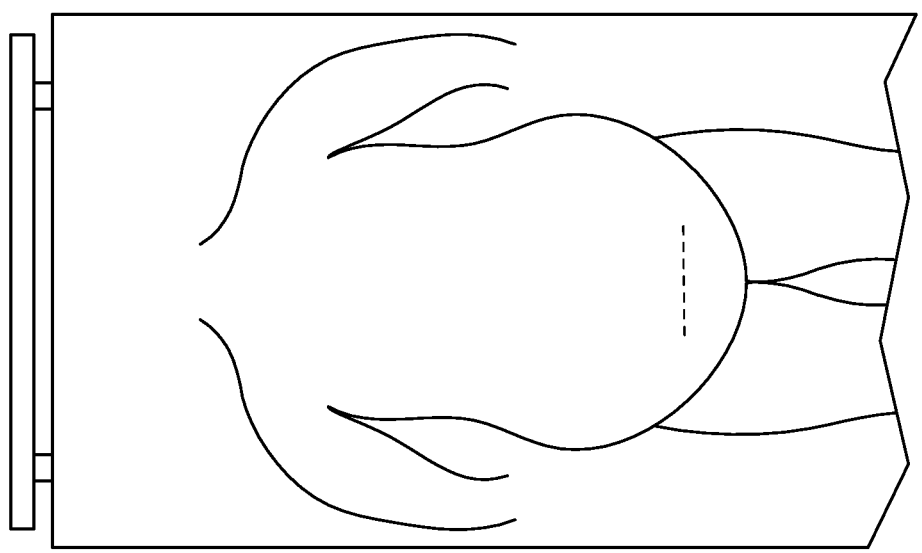
FIG. 1A is an example of a patient with a pannus having an incision site obscured by the pannus.
Figure 1C:
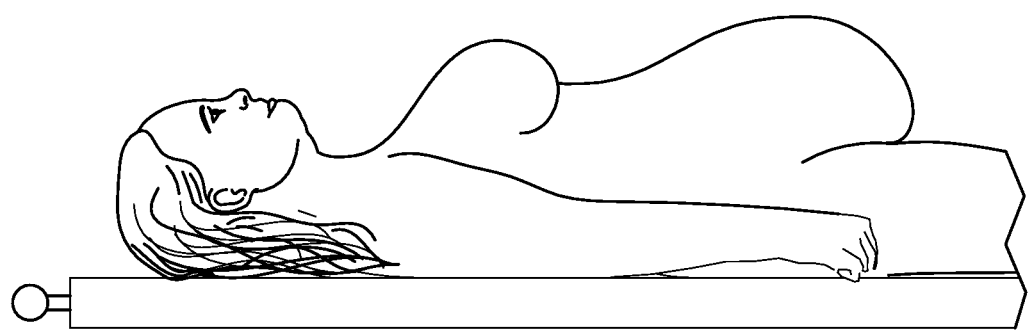
FIG. 1C is side view of a patient with a pannus having an incision site obscured by the pannus.
Figure 1D:
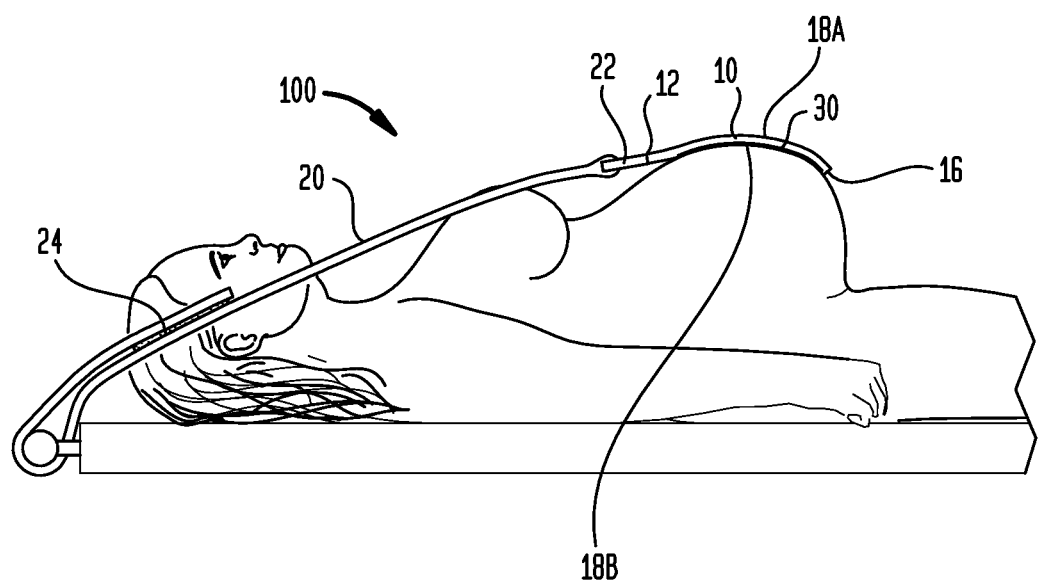
FIG. 1D is side view of the abdominal elevator retracting the pannus to expose the incision site.

When fully assembled, the abdominal elevator (100) has a length (L3) that is sufficient to allow the body portion (10) to attach to the pannus via the adhesive layer (30) and to the bedrail via the straps (20). After placement of the body portion (10) via the adhesive layer (30), light to moderate traction is applied to the abdominal wall causing elevation of the pannus. The pannus is restrained with one or more straps (20) that are attached to the bedrail either along the top of the bed as shown in FIGS. 1B and 1D or at the side of the bedrail if straps (20) are attached at the side of the body portion (10).

The adhesive (30) may be covered by a release liner (not shown). The release liner may be selected from the group consisting of a polymer, paper, coated paper, and a silicone coated paper.

The abdominal elevator (100) may be manufactured by forming the shape of the body portion (10) of the device from a polymer, paper, or cloth, laminating an adhesive (30) onto the body portion of the device and laminating a release sheet onto the adhesive (30) and attaching the straps (20) to the body portion (10). Alternatively, the abdominal elevator (100) may be manufactured by extruding a thin film to form the body portion (10), laminating an adhesive (30) onto the body portion, laminating a release sheet onto the adhesive (30), and attaching the straps (20) using a connector (22) or attacher (24).

The abdominal elevator is made sterile in any number of ways including, formulating the body portion (10) and straps (20) from a sterile component, applying an antimicrobial adhesive (30) to the posterior surface (18b) of the body portion (10), or sterilizing the entire device (100) through an acceptable process such as ethylene oxide, gamma irradiation, or electron beam radiation, or any combination thereof.

Although the present invention has been described with reference to numerous embodiments, the foregoing description is intended to be merely illustrative. Numerous other arrangements and configurations can be readily devised by those skilled in the art without departing from the spirit and scope of the present invention as defined by the following claims.

I claim:

1. An abdominal elevator comprising:
   a. a sterile transparent flexible body portion having an anterior surface and posterior surface and at least one upper edge defined between the anterior and posterior surfaces, or optionally two or more side edges, with one or more straps that may be continuous with the transparent flexible body portion or reliably secured only along the edge without substantial overlap with the anterior or posterior surfaces of the body portion by welding, gluing, tying, sewing, an connector, or an attacher, wherein the straps being an adjustable length allow attachment to a bedrail to effect retraction by elevation of a pannus from the surgical site, and
   b. a medical grade adhesive applied to the posterior surface of the transparent flexible body portion to effect secure attachment of the transparent flexible body portion to the pannus, and
   c. optionally, a release sheet applied to the adhesive,
   d. wherein light to moderate traction is applied to said sterile abdominal elevator to elevate said pannus from the surgical site.

2. The abdominal elevator of claim 1, wherein the body portion is of a geometric shape selected from the shape consisting of a triangle, rectangle, oval or other suitable shape for securely containing a pannus.

3. The abdominal elevator of claim 2, wherein the edges of the geometric shape are rounded to impart more comfort to the patient.

4. The abdominal elevator of claim 1, wherein the body portion has a width of about 50 to 100 cm.

5. The abdominal elevator of claim 1, wherein the body portion has a height of 20 to 80 cm.

6. The abdominal elevator of claim 1, wherein the body portion is made from a strong and durable material selected from the group consisting of foam, paper, a polymer or cloth.

7. The abdominal elevator of claim 6, wherein when the body portion is made from a polymer, the polymer is selected from the group consisting of polyethylenes, polyurethanes, polyesters and polyamides.

8. The abdominal elevator of claim 1, wherein the body portion is made from a material containing an antimicrobial component.

9. The abdominal elevator of claim 1, having one strap attached to the upper edge of the body portion.

10. The abdominal elevator of claim 1, having two straps attached to the side edges of the body portion.

11. The abdominal elevator of claim 1, having three straps attached to each of the upper edge and each side edge of the body portion.

12. The abdominal elevator of claim 1, wherein the straps are made of any sturdy material selected from the group consisting of foam, paper, a polymer or cloth.

13. The abdominal elevator of claim 1, wherein the length of said strap are 140 to 170 cm.

14. The abdominal elevator of claim 1, wherein the adhesive is a pressure sensitive adhesive.

15. The abdominal elevator of claim 14, wherein the adhesive contains an antimicrobial selected from the group consisting of iodine, phenols, fatty acid monoesters, silver, silver salts and hydrogen peroxide.

16. A method of retracting an abdominal pannus comprising the steps of:
   a. attaching a sterile abdominal elevator at a transparent flexible body portion to an abdominal pannus using a medical grade adhesive, the flexible body portion having an anterior surface and posterior surface and at least one upper edge defined between the anterior and posterior surfaces, or optionally two or more side edges, with one or more straps that may be continuous with the transparent flexible body portion or reliably secured only along the edge without substantial overlap with the anterior or posterior surfaces of the body portion by welding gluing, tying, sewing, a connector, or an attacher, wherein the straps being an adjustable length allow attachment to a bedrail to effect retraction by elevation of a pannus from the surgical site, and the medical grade adhesive applied to the posterior surface of the transparent flexible body portion;
   b. applying light to moderate traction to the abdominal elevator to elevate the pannus from a surgical site;
   c. retracting the abdominal pannus with the sterile abdominal elevator by securing the adjustable straps from the sterile abdominal elevator to a bedrail above a patient's head or at the patient's side.

17. A method of making an abdominal elevator comprising the steps of:
   a. forming a flexible body portion of an abdominal elevator from a transparent strong and durable material, the flexible body portion having an anterior surface and posterior surface and at least one upper edge defined between the anterior and posterior surfaces, or optionally two or more side edges, comprising straps that are either continuous with the flexible body portion or reliably secured along on or more edges of the body portion without substantial overlap with the anterior or posterior surfaces of the body portion by welding gluing, tying, sewing, a connector, or an attacher, wherein the straps being an adjustable length allow attachment to a bedrail to effect retraction by elevation of a pannus from the surgical site;
   b. applying a medical grade adhesive onto the posterior surface of the transparent flexible body portion; and
   c. sterilizing the abdominal elevator; or
   d. optionally, laminating a release sheet on the adhesive.

18. A method of claim 17, further comprising the steps of sterilizing the abdominal elevator using ethylene oxide, gamma irradiation, electron beam radiation or a combination thereto.

* * * * *